United States Patent
Kashima

(10) Patent No.: US 10,292,385 B2
(45) Date of Patent: May 21, 2019

(54) METHOD FOR SUPRESSION OF INFECTION BY PLANT VIRUS

(71) Applicant: ISHIHARA SANGYO KAISHA, LTD., Osaka-shi, Osaka (JP)

(72) Inventor: Takayuki Kashima, Kusatsu (JP)

(73) Assignee: ISHIHARA SANGYO KAISHA, LTD., Osaka-Shi, Osaka (JP)

( * ) Notice: Subject to any disclaimer, the term of this patent is extended or adjusted under 35 U.S.C. 154(b) by 150 days.

(21) Appl. No.: 15/129,178

(22) PCT Filed: Mar. 27, 2015

(86) PCT No.: PCT/JP2015/059632
§ 371 (c)(1),
(2) Date: Sep. 26, 2016

(87) PCT Pub. No.: WO2015/147263
PCT Pub. Date: Oct. 1, 2015

(65) Prior Publication Data
US 2018/0177186 A1 Jun. 28, 2018

(30) Foreign Application Priority Data

Mar. 28, 2014 (JP) .................. 2014-068268

(51) Int. Cl.
| | | |
|---|---|---|
| *A61K 31/44* | (2006.01) | |
| *A01N 37/02* | (2006.01) | |
| *A01N 25/02* | (2006.01) | |
| *A01N 43/22* | (2006.01) | |
| *A01N 43/40* | (2006.01) | |
| *A01N 43/56* | (2006.01) | |
| *A01N 43/58* | (2006.01) | |
| *A01N 43/88* | (2006.01) | |

(52) U.S. Cl.
CPC ............. *A01N 37/02* (2013.01); *A01N 25/02* (2013.01); *A01N 43/22* (2013.01); *A01N 43/40* (2013.01); *A01N 43/56* (2013.01); *A01N 43/58* (2013.01); *A01N 43/88* (2013.01)

(58) Field of Classification Search
CPC .................................................. A01N 37/02

USPC ........................................................ 514/357
See application file for complete search history.

(56) References Cited

U.S. PATENT DOCUMENTS

| 6,294,578 B1 * | 9/2001 | Arimoto ................. A01N 37/02 514/506 |
| 8,404,260 B2 * | 3/2013 | Reid ...................... A01N 43/40 424/405 |
| 2001/0034368 A1 | 10/2001 | Arimoto et al. |
| 2007/0190096 A1 * | 8/2007 | Arimoto ................. A01N 37/06 424/405 |
| 2007/0299264 A1 | 12/2007 | Huang et al. |
| 2011/0196001 A1 | 8/2011 | Huang et al. |
| 2013/0123307 A1 | 5/2013 | Huang et al. |
| 2013/0212744 A1 | 8/2013 | Monir et al. |

FOREIGN PATENT DOCUMENTS

| JP | 10-251104 A | 9/1998 |
| JP | 2006-232709 A | 9/2006 |
| JP | 2009-541313 A | 11/2009 |
| JP | 2013-525395 A | 6/2013 |
| WO | WO 2006/028170 A1 | 3/2016 |

OTHER PUBLICATIONS

Kashima et al., Journal of Pesticide Science, 2014, 39(1-2):91-97.*
International Search Report (PCT/ISA/210) dated May 19, 2015, by the Japan Patent Office as the International Searching Authority for International Application No. PCT/JP2015/059632.
Written Opinion (PCT/ISA/237) dated May 19, 2015, by the Japan Patent Office as the International Searching Authority for International Application No. PCT/JP2015/059632.
Kashima et al., "Effect of a novel repellent, acetylated glyceride, against sweet potato whitefly, Bemisia tabaci (Gennadius) ( Hemiptera:Aleyrodidae)", Journal of Pesticidal Science, Apr. 27, 2014, V39, p. 91-97.

* cited by examiner

*Primary Examiner* — Rei Tsang Shiao
(74) *Attorney, Agent, or Firm* — Buchanan, Ingersoll & Rooney PC

(57) ABSTRACT

The present invention provides: a composition containing (a) a glycerin acetic acid fatty acid ester and (b) a particular insecticidal compound; and a method for suppressing plant virus infection transmitted by winged pests, the method including applying the composition to a crop.

16 Claims, No Drawings

METHOD FOR SUPRESSION OF INFECTION BY PLANT VIRUS

TECHNICAL FIELD

The present invention relates to a method for suppressing plant virus infection transmitted by winged pests.

BACKGROUND ART

Patent Literature 1 describes: winged pest repellents containing as an active ingredient at least one selected from glycerin fatty acid ester, sorbitan fatty acid ester, acetylated monoglyceride, organic acid monoglyceride, propylene glycol fatty acid ester, polyoxyethylene sorbitan, fatty acid, sucrose fatty acid ester, sorbitan, and soybean oil-based fatty acid methyl ester; and methods for repelling winged pests using the repellents.

However, Patent Literature 1 fails to disclose a combination(s) of a compound A, which is an active ingredient of the present invention, with a particular insecticidal compound(s), and does not disclose that the combination(s) are capable of suppressing plant virus infection transmitted by winged pests.

CITATION LIST

Patent Literature

Patent Literature 1: International Publication No. WO2006/028170

SUMMARY OF INVENTION

Technical Problems

At present, practical fields of agriculture have serious problems of plant virus infection of crops such as cucumber, eggplant, garlic chives, radish, cherry tomato, and tomato. Nevertheless, effective means for curing the crops infected with plant viruses has not been established satisfactorily.

In addition, there are many types of winged pests transmitting the virus. Recently, winged pests (resistant winged pests) have emerged which are less sensitive to agrochemical insecticides. For these reasons, it can hardly be said that there are effective measures against the plant virus transmission. An object of the present invention is to provide a method for remarkably suppressing plant virus infection, and to provide a composition used in the infection suppression method.

Solution to Problems

As a result of studies to solve the above-described problems, the present inventor has found that a combination(s) of particular compounds, which are active ingredients of the present invention, have an unexpectedly excellent effect of suppressing plant virus infection in comparison with a case of applying each of the compounds alone. Based on the finding thus obtained, the present invention has been completed.

Specifically, the present invention relates to a method for suppressing plant virus infection transmitted by winged pests, the method comprising applying, to a crop, (a) an effective amount of a glycerin acetic acid fatty acid ester (hereinafter abbreviated as compound A) and (b) an effective amount of at least one insecticidal compound (hereinafter abbreviated as compound B) selected from the group consisting of nitenpyram, dinotefuran, pyridaben, spiromesifen, buprofezin, fenpyroximate, acetamiprid, milbemectin, tolfenpyrad, flonicamid, pymetrozine, pyrifluquinazone, clothianidin, imidacloprid, thiamethoxam, sulfoxaflor, pyridalyl, cyclaniliprole, chlorantraniliprole, cyantraniliprole, fenpropathrin, fenitrothion, ethofenprox, teflubenzuron, thiacloprid, lufenuron, spirotetramat, pyriproxifen, hydroxypropyl starch, saccharified reduced starch, fatty acid triglycerides containing a fatty acid having 8 to 18 carbon atoms as a constituent fatty acid (the constituent fatty acid is preferably a fatty acid having 8 to 12 carbon atoms, more preferably a fatty acid having 8 to 10 carbon atoms), sodium oleate, flupyradifurone, triflumezopyrim, MSI-1302, AKD-1193, NC-515, MIE-1209, spinetoram, pirimiphos-methyl, emamectin benzoate, methidathion, chinomethionate, cartap, thiocyclam, spinosad, novaluron, lepimectin, acequinocyl, fenbutatin oxide, tebufenpyrad, DBEDC, chlorfluazuron, and salts thereof. Moreover, the present invention relates to a composition for suppressing plant virus infection transmitted by winged pests, the composition comprising the compound A and the compound B as active ingredients.

Advantageous Effects of Invention

The method for suppressing plant virus infection transmitted by winged pests and the composition for suppressing plant virus infection transmitted by winged pests, which are provided by the present invention, surprisingly make it possible to remarkably suppress plant virus infection of crops. The present invention as described above is very effective against infection of crops with "plant viruses" which are quite difficult to control and suppress, and which greatly influence crop yield and so forth. The difficulty in controlling and suppressing the infection is as described in the explanation of the "plant viruses" to be described later. The present invention exhibits quite an effective effect with small amounts of the chemicals in comparison with a case of applying a single chemical used with an expectation of certain effects at actual sites. Accordingly, the present invention is effective also in reducing the environmental load to the application area or the surroundings. The effects of the present invention are such that a percentage of infection suppressed in the case of combining two active ingredients is higher than a percentage of infection suppressed, which is predicted from percentages of infection suppressed by the two respective active ingredients, making it possible to remarkably suppress plant virus infection.

DESCRIPTION OF EMBODIMENTS

In the present invention, examples of a "plant virus" include: the genus *Begomovirus* such as tomato yellow leaf curl virus (TYLCV), tobacco leaf curl Japan virus (TbLCJV), and honeysuckle yellow vein mosaic virus (HYVMV); the genus *Crinivirus* such as cucurbit chlorotic yellows virus (CCYV), tomato infectious chlorosis virus (TICV), tomato chlorosis virus (ToCV), cucurbit yellow stunting disorder virus (CYSDV), lettuce infectious yellows virus (LIYV), and beet pseudo yellow virus (BPYV); the genus *Potyvirus* such as papaya ringspot virus (PRSV), watermelon mosaic virus (WMV), zucchini yellow mosaic virus (ZYMV), potato virus Y (PVY), tulip breaking virus (TBV), cucumber vein yellowing virus (CVYV), and sweet potato mild virus (SPMMV); the genus *Tospovirus* such as tomato spotted wilt virus (TSWV), watermelon silver mottle virus (WSMoV), melon yellow spot virus (MYSV), impatiens necrotic spot virus (INSV), iris yellow spot virus (IYSV), capsicum chlorosis virus (CaCV), and chrysanthemum stem necrosis virus (CSNV); and the like.

Among these plant viruses, those mainly transmitted by whiteflies include TYLCV, TbLCJV, HYVMV, BPYV, CCYV, TICV, ToCV, CYSDV, LIYV, CVYV, SPMMV, and the like.

Moreover, those mainly transmitted by thrips include TSWV, WSMoV, MYSV, INSV, IYSV, CaCV, CSNV, and the like.

Further, those mainly transmitted by aphids include PRSV, WMV, ZYMV, PVY, TBV, and the like.

The present invention is particularly effective in suppressing the plant viruses transmitted by whiteflies. Above all, tomato yellow leaf curl virus (TYLCV) is particularly effectively suppressed.

Tomato yellow leaf curl virus (TYLCV) is a plant virus mediated by adult sweet potato whiteflies (*Bemisia tabaci*). Once the infection occurs, there is no curing means, so that the virus causes serious problems worldwide. Adult sweetpotato whiteflies generally fly onto a leave of a plant to be infected, and then moves to the underleaf, where the whiteflies suck a phloem sap and mate. Once adults are settled on an underleaf, they hardly move unless there is a great stimulus such as strong vibration. It is known that when an adult sweetpotato whitefly sucks a phloem sap, TYLCV enters a plant body together with saliva secreted in this event, so that the plant virus infects the plant. For this infection to occur, a certain amount of the plant virus needs to be incorporated into a plant body. Nevertheless, TYLCV infects a plant as quickly as approximately 15 minutes after an adult sweetpotato whitefly starts sucking the phloem sap.

Hence, even if already-existing insecticides such as nitenpyram, which have been conventionally used to control adult sweetpotato whiteflies resistant to chemicals such as organophosphorus insecticides, carbamate insecticides, synthetic pyrethroid insecticides, ecdysis regulating insecticides, and neonicotinoid insecticides, the virus infection has not been sufficiently suppressed in a case of a high infection pressure, since time is required to exhibit the insecticidal effects against such adult sweetpotato whiteflies.

A compound A is known as a food additive. An example thereof includes a compound represented by the following formula (I):

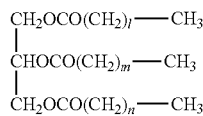
(I)

(in the formula, l is an integer of 0 to 16; m is an integer of 0 to 16; n is an integer of 0 to 16; and one or two of l, m, and n are 0 (excluding a case where all of l, m, and n are 0)).

The compound A is preferably the compound represented by the formula (I) where one or two of l, m, and n are 0, more preferably the compound where one or two of l, m, and n are 0 while one of the remaining is 6 to 16, and particularly preferably the compound where one or two of l, m, and n are 0 while one of the remaining is 10 (i.e., glycerin diacetomonolaurate).

A compound B is an agrochemical. The compound B includes the following.

(I) nitenpyram (common name) which is a compound described on pp. 817 to 818 of The Pesticide Manual (15th ed.; BRITISH CROP PROTECTION COUNCIL).

(II) dinotefuran (common name) which is a compound described on pp. 391 to 392 of The Pesticide Manual (15th ed.; BRITISH CROP PROTECTION COUNCIL).

(III) pyridaben (common name) which is a compound described on pp. 986 to 987 of The Pesticide Manual (15th ed.; BRITISH CROP PROTECTION COUNCIL).

(IV) spiromesifen (common name) which is a compound described on pp. 1046 to 1047 of The Pesticide Manual (15th ed.; BRITISH CROP PROTECTION COUNCIL).

(V) buprofezin (common name) which is a compound described on pp. 138 to 139 of The Pesticide Manual (15th ed.; BRITISH CROP PROTECTION COUNCIL).

(VI) fenpyroximate (common name) which is a compound described on pp. 488 to 489 of The Pesticide Manual (15th ed.; BRITISH CROP PROTECTION COUNCIL).

(VII) acetamiprid (common name) which is a compound described on pp. 9 to 10 of The Pesticide Manual (15th ed.; BRITISH CROP PROTECTION COUNCIL).

(VIII) milbemectin (common name) which is a compound described on pp. 793 to 794 of The Pesticide Manual (15th ed.; BRITISH CROP PROTECTION COUNCIL).

(IX) tolfenpyrad (common name) which is a compound described on pp. 1136 to 1137 of The Pesticide Manual (15th ed.; BRITISH CROP PROTECTION COUNCIL).

(X) flonicamid (common name) which is a compound described on pp. 507 to 508 of The Pesticide Manual (15th ed.; BRITISH CROP PROTECTION COUNCIL).

(XI) pymetrozine (common name) which is a compound described on pp. 968 to 969 of The Pesticide Manual (15th ed.; BRITISH CROP PROTECTION COUNCIL).

(XII) pyrifluquinazone (common name) which is a compound described on p. 992 of The Pesticide Manual (15th ed.; BRITISH CROP PROTECTION COUNCIL).

clothianidin (common name) which is a compound described on pp. 225 to 226 of The Pesticide Manual (16th ed.; BRITISH CROP PROTECTION COUNCIL).

imidacloprid (common name) which is a compound described on pp. 640 to 642 of The Pesticide Manual (16th ed.; BRITISH CROP PROTECTION COUNCIL).

thiamethoxam which is a compound described on pp. 1104 to 1105 of The Pesticide Manual (16th ed.; BRITISH CROP PROTECTION COUNCIL).

sulfoxaflor (common name) which is a compound described on pp. 1057 to 1058 of The Pesticide Manual (16th ed.; BRITISH CROP PROTECTION COUNCIL).

pyridalyl (common name) which is a compound described on pp. 981 to 982 of The Pesticide Manual (16th ed.; BRITISH CROP PROTECTION COUNCIL).

cyclaniliprole (common name) which is a compound described as compound No. 16 in International Publication No. WO2005/077934.

chlorantraniliprole (common name) which is a compound described on pp. 172 to 173 of The Pesticide Manual (16th ed.; BRITISH CROP PROTECTION COUNCIL).

cyantraniliprole (common name) which is a compound described on pp. 247 to 248 of The Pesticide Manual (16th ed.; BRITISH CROP PROTECTION COUNCIL).

fenpropathrin (common name) which is a compound described on pp. 474 to 475 of The Pesticide Manual (16th ed.; BRITISH CROP PROTECTION COUNCIL).

fenitrothion (common name) which is a compound described on pp. 465 to 466 of The Pesticide Manual (16th ed.; BRITISH CROP PROTECTION COUNCIL).

ethofenprox (common name) which is a compound described on pp. 445 to 446 of The Pesticide Manual (16th ed.; BRITISH CROP PROTECTION COUNCIL).

teflubenzuron (common name) which is a compound described on pp. 1073 to 1074 of The Pesticide Manual (16th ed.; BRITISH CROP PROTECTION COUNCIL).

thiacloprid (common name) which is a compound described on pp. 1102 to 1103 of The Pesticide Manual (16th ed.; BRITISH CROP PROTECTION COUNCIL).

lufenuron (common name) which is a compound described on pp. 692 to 693 of The Pesticide Manual (16th ed.; BRITISH CROP PROTECTION COUNCIL).

spirotetramat (common name) which is a compound described on pp. 1042 to 1043 of The Pesticide Manual (16th ed.; BRITISH CROP PROTECTION COUNCIL).

pyriproxifen (common name) which is a compound described on pp. 992 to 993 of The Pesticide Manual (16th ed.; BRITISH CROP PROTECTION COUNCIL).

flupyradifurone (common name) which is a compound described on p. 536 of The Pesticide Manual (16th ed.; BRITISH CROP PROTECTION COUNCIL).

triflumezopyrim (common name) which is a compound known under the IUPAC name of 3,4-dihydro-2,4-dioxo-1-(pyrimidin-5-ylmethyl)-3-($\alpha,\alpha,\alpha$-trifluoro-m-tolyl)-2H-pyrido[1,2-a]pyrimidin-1-ium-3-ide.

MSI-1302, AKD-1193, NC-515, and MIE-1209 which are contract test codes of chemicals (novel compounds) described in Shinnouyaku Jitsuyoukashiken Seisekisyuu (rice, vegetables, etc.) and insect damage control (III the Hokuriku region) in 2014 by Japan Plant Protection Association (issued on Nov. 4, 2014). Additionally, NC-515 is a compound described also in Japanese Patent Application Publication No. 2015-44791.

spinetoram (common name) which is a compound described on pp. 1034 to 1035 of The Pesticide Manual (16th ed.; BRITISH CROP PROTECTION COUNCIL).

pirimiphos-methyl (common name) which is a compound described on pp. 909 to 910 of The Pesticide Manual (16th ed.; BRITISH CROP PROTECTION COUNCIL).

emamectin benzoate (common name) which is a compound described on pp. 410 to 411 of The Pesticide Manual (16th ed.; BRITISH CROP PROTECTION COUNCIL).

methidathion (common name) which is a compound described on pp. 748 to 749 of The Pesticide Manual (16th ed.; BRITISH CROP PROTECTION COUNCIL).

chinomethionate (common name) which is a compound known under the IUPAC name of 6-methyl-1,3-dithiolo[4,5-b]guinoxalin-2-one.

Cartap (common name) which is a compound described on pp. 166 to 167 of The Pesticide Manual (16th ed.; BRITISH CROP PROTECTION COUNCIL).

thiocyclam (common name) which is a compound described on pp. 1114 to 1115 of The Pesticide Manual (16th ed.; BRITISH CROP PROTECTION COUNCIL).

spinosad (common name) which is a compound described on pp. 1036 to 1038 of The Pesticide Manual (16th ed.; BRITISH CROP PROTECTION COUNCIL).

novaluron (common name) which is a compound described on pp. 818 to 819 of The Pesticide Manual (16th ed.; BRITISH CROP PROTECTION COUNCIL).

lepimectin (common name) which is a compound described on pp. 689 to 690 of The Pesticide Manual (16th ed.; BRITISH CROP PROTECTION COUNCIL).

acequinocyl (common name) which is a compound described on pp. 7 to 9 of The Pesticide Manual (16th ed.; BRITISH CROP PROTECTION COUNCIL).

fenbutatin oxide (common name) which is a compound described on pp. 460 to 461 of The Pesticide Manual (16th ed.; BRITISH CROP PROTECTION COUNCIL).

tebufenpyrad (common name) which is a compound described on pp. 1067 to 1068 of The Pesticide Manual (16th ed.; BRITISH CROP PROTECTION COUNCIL).

DBEDC (common name) which is a compound known under a chemical name of dodecylbenzenesulfonic acid bisethylenediamine copper complex salt (II).

chlorfluazuron (common name) which is a compound described on pp. 179 to 180 of The Pesticide Manual (16th ed.; BRITISH CROP PROTECTION COUNCIL).

Among these, (I) nitenpyram, (II) dinotefuran, (III) pyridaben, (X) flonicamid, (XI) pymetrozine, and (XII) pyrifluquinazone are compounds generally used as adulticides. Meanwhile, (IV) spiromesifen, (V) buprofezin, (VI) fenpyroximate, (VII) acetamiprid, (VIII) milbemectin, and (IX) tolfenpyrad are compounds generally used as ovicides or larvicides. Quite unexpectedly, the present invention demonstrates an effect of suppressing plant virus infection synergistically in combination with such compounds used as ovicides or larvicides.

Among the compounds B described above, preferable for more remarkably exhibiting the effects of the present invention is at least one selected from the group consisting of nitenpyram, dinotefuran, pyridaben, spiromesifen, buprofezin, fenpyroximate, acetamiprid, milbemectin, tolfenpyrad, flonicamid, pymetrozine, and pyrifluquinazone. More preferable is at least one selected from the group consisting of (I) nitenpyram, (II) dinotefuran, (III) pyridaben, (IV) spiromesifen, (V) buprofezin, (VI) fenpyroximate, (VII) acetamiprid, (VIII) milbemectin, and (IX) tolfenpyrad. Further preferable is at least one selected from the group consisting of (I) nitenpyram, (III) pyridaben, (V) buprofezin, (VI) fenpyroximate, and (VIII) milbemectin. Furthermore preferably, a mixture of (V) buprofezin and (VI) fenpyroximate is used.

The compound B includes compounds that can form a salt. The salt may be any agriculturally acceptable salt. Examples thereof include: alkali metal salts such as sodium salts and potassium salts; alkaline earth metal salts such as magnesium salts and calcium salts; ammonium salts such as monomethylammonium salts, dimethylammonium salts, and triethylammonium salts; inorganic acid salts such as hydrochlorides, perchlorates, sulfates, and nitrates; organic acid salts such as acetates and methanesulfonates; and the like.

A mixing ratio of each compound in the present invention cannot be generally specified because it is necessary to adjust the mixing ratio as appropriate depending on the formulation form, the weather condition, and the like. Nonetheless, the mixing ratio of the compound A and the compound B is, for example, 1:30 to 25,600:1, desirably 1:16 to 6,400:1, more desirably 1:8 to 1600:1, and furthermore desirably 1:4 to 240:1, by the weight ratio.

Amounts of the compound A and the compound B contained in the composition should be adjusted as appropriate depending on the mixing ratio of each compound, the formulation form, the weather condition, and the like. Moreover, the compound A and the compound B may be diluted with water or the like at the time of the application.

The amount of the compound A at the time of the application to a crop is preferably 400 to 12,800 ppm, more preferably 500 to 6,400 ppm, furthermore preferably 800 to 3,000 ppm, and particularly preferably 1,000 to 2,000 ppm. Alternatively, the amount may be 1,600 to 6,400 ppm. Similarly, the amount of the compound B at the time of the application to a crop is preferably 0.5 to 12,000 ppm, more preferably 1 to 6,000 ppm, furthermore preferably 2 to 3,000 ppm, furthermore preferably 3 to 1,000 ppm, and particularly preferably 5 to 500 ppm.

In the present invention, the "application" can be performed on a "crop" or a "crop part" affected by winged pests transmitting plant viruses, by any known method such as spraying and soil treatment. The application timing is not particularly limited, but the composition is preferably applied in advance before winged pests fly to the crop.

In the present invention, the "crop" includes eggplant (*Solanum melongena*), cucumber (*Cucumis sativus*), tomato (*Solanum lycopersicum*), cherry tomato (*Solanum lycopersicum* var. cerasiforme), and the like, but is preferably tomato and cherry tomato. The "crop part" means any portion of the crop and includes roots, stems, branches, leaves, flowers, and the like of the crop. Now, the crop will be described in detail. It should be understood that the crop means all crops such as desired harvest crops and undesired wild crops or harvest crops (including naturally growing harvest crops). The crop may be crops that can be obtained by traditional breeding techniques and optimization techniques. Moreover, the crop may be crops that can be obtained by biotechnology techniques and recombination techniques. Further, the crop includes transgenic plants.

In the present invention, examples of the "winged pests" transmitting plant viruses include whiteflies such as sweetpotato whitefly and greenhouse whitefly (*Trialeurodes vaporariorum*); thrips such as yellow tea thrips (*Scirtothrips dorsalis*), melon thrips (*Thripspalmi*), western flower thrips (*Frankliniella occidentalis*), onion thrips (*Thrips tabaci*), and flower thrips (*Frankliniella intonsa*); aphids such as cotton aphid (*Aphis gossypii*) and green peach aphid (*Myzus persicae*); and the like. Among these, the present invention is effective against plant viruses transmitted by whiteflies. The present invention is particularly effective against plant viruses transmitted by sweetpotato whitefly among the whiteflies.

Here, the "winged pests" transmitting plant viruses also include winged pests having tolerance to insecticides such as neonicotinoid compounds and synthetic pyrethroid compounds (resistant winged pests), and further include winged pests having cross tolerance or multi-chemical tolerance.

In addition, in the present invention, "suppress" and related terms mean to mitigate the degree of plant virus infection. It is a matter of course that the terms include completely controlling plant virus infection.

As long as the object of the present invention is met, the active ingredients described above can be used in mixture or combination with other herbicides, fungicides, antibiotics, plant hormones, insecticides, fertilizers, safeners, or the like in consideration of the pests or a place where they grow. In such cases, more excellent effects and actions may be exhibited.

The composition of the present invention can be prepared by blending the active ingredients of the compound A and the compound B with various adjuvants in accordance with normal methods for formulating agricultural chemicals, and applied in various formulation forms such as powder, granule, water dispersible granule, wettable powder, tablet, pill, capsule (including a form packaged by a water soluble film), water-based suspension, oil-based suspension, microemulsion formulation, suspoemulsion formulation, wettable powder, emulsion, liquid, and paste. As long as the object of the present invention is met, the composition may be in any formulation form normally used in the art.

In preparing such formulations, a formulation may be prepared by mixing the compound A and the compound B together, or a formulation of compound A and a formulation of compound B maybe prepared separately and these may be mixed at the time of the application.

The adjuvants used in the formulation include solid carriers such as kaolinite, sericite, diatomaceous earth, slaked lime, calcium carbonate, talc, white carbon, kaoline, bentonite, clay, sodium carbonate, sodium bicarbonate, mirabilite, zeolite, and starches; solvents such as water, toluene, xylene, solvent naphtha, dioxane, dimethylsulfoxide, N,N-dimethylformamide, dimethylacetamide, N-methyl-2-pyrrolidone, and alcohols; anionic surfactants such as fatty acid salts, benzoates, polycarboxylate, alkylsulfuric acid ester salts, alkyl sulfates, alkylaryl sulfates, alkyl diglycol ether sulfates, alcohol sulfuric acid ester salts, alkyl sulfonates, alkylaryl sulfonates, aryl sulfonates, lignin sulfonates, alkyldiphenyl ether disulfonates, polystyrene sulfonates, alkyl phosphoric acid ester salts, alkylaryl phosphates, styrylaryl phosphates, polyoxyethylene alkyl ether sulfuric acid ester salts, polyoxyethylene alkylaryl ether sulfates, polyoxyethylene alkylaryl ether sulfuric acid ester salts, polyoxyethylene alkyl ether phosphates, polyoxyethylene alkylaryl phosphoric acid ester salts, polyoxyethylene aryl ether phosphoric acid ester salts, naphthalenesulfonic acid-formalin condensates, and salts of alkyl naphthalenesulfonic acid-formalin condensates; nonionic surfactants such as sorbitan fatty acid esters, diglycerin fatty acid esters, triglycerin fatty acid esters, fatty acid polyglycerides, fatty acid alcohol polyglycol ethers, acetylene glycols, acetylene alcohols, oxyalkylene block polymers, polyoxyethylene alkyl ethers, polyoxyethylene alkylaryl ethers, polyoxyethylene styrylaryl ethers, polyoxyethylene glycol alkyl ethers, polyethylene glycols, polyoxyethylene fatty acid esters, polyoxyethylene sorbitan fatty acid esters, polyoxyethylene glycerin fatty acid esters, polyoxyethylene hydrogenated castor oils, and polyoxypropylene fatty acid esters; vegetable oils and mineral oils such as olive oil, kapok oil, castor oil, palm oil, camellia oil, coconut oil, sesame oil, corn oil, rice bran oil, peanut oil, cottonseed oil, soybean oil, rapeseed oil, linseed oil, tung oil, and liquid paraffins; transesterified vegetable oils such as methylated rapeseed oil and ethylated rapeseed oil; and the like.

One of each ingredient of these adjuvants can be used alone or two or more can be used in combination, as long as the object of the present invention is met. Moreover, adjuvants other than those described above can also be used by selecting it from among adjuvants known in the art. For example, it is also possible to use normally used various adjuvants such as a filler, a thickener, an anti-settling agent, an anti-freezing agent, a dispersion stabilizer, a safener, an anti-mold agent, a foaming agent, a disintegrator, and a binder. A blending ratio by weight of the active ingredients and various adjuvants in the composition of the present invention may be 0.001:99.999 to 95:5, desirably approximately 0.1:99.9 to 90:10, and further desirably 1:99 to 80:20.

As the method for applying the composition of the present invention, various methods can be employed. The method can be selected for use as appropriate depending on various conditions such as the application site, the formulation form, and the type and growth stage of undesired crop. Examples of the method include the following.

1. A formulation prepared by mixing the compound A and the compound B together is applied as it is.
2. A formulation prepared by mixing the compound A and the compound B together is diluted to a predetermined concentration with water or the like, mixed as necessary with various spreaders (such as surfactant, vegetable oil, mineral oil), and applied.
3. Formulations separately prepared from the compound A and the compound B are applied as they are.
4. Formulations prepared separately from the compound A and the compound B are diluted as necessary to predetermined concentrations with water or the like, mixed as necessary with various spreaders (such as surfactant, vegetable oil, mineral oil), and applied.
5. Formulations prepared separately from the compound A and the compound B are mixed with each other when diluted to predetermined concentrations with water or the like, mixed as necessary with various spreaders (such as surfactant, vegetable oil, mineral oil), and applied.

Examples of desired embodiments of the present invention will be described below. However, the present invention is by no means limited thereto.

(1) A composition for suppressing plant virus infection transmitted by winged pests, the composition comprising: (a) a glycerin acetic acid fatty acid ester; and (b) at least one insecticidal compound selected from the group consisting of nitenpyram, dinotefuran, pyridaben, spiromesifen, buprofezin, fenpyroximate, acetamiprid, milbemectin, tolfenpyrad, flonicamid, pymetrozine, pyrifluquinazone and salts thereof.
(2) The composition according to (1), wherein (b) is nitenpyram, dinotefuran, pyridaben, spiromesifen, buprofezin, fenpyroximate, acetamiprid, milbemectin, tolfenpyrad, or a salt thereof.
(3) The composition according to (1), wherein (b) is nitenpyram, pyridaben, buprofezin, fenpyroximate, milbemectin, or a salt thereof.
(4) The composition according to (1), wherein (b) is buprofezin and fenpyroximate or salt(s) thereof.
(5) The composition according to (1), wherein the winged pests are whiteflies.
(6) The composition according to (1), wherein the winged pests are sweetpotato whiteflies.
(7) The composition according to (1), wherein the winged pests are resistant sweetpotato whiteflies.
(8) The composition according to (1), wherein the plant virus is Tomato yellow leaf curl virus.
(9) The composition according to (1), comprising (a) and (b) in amounts (synergistic effective amounts) to exhibit a synergistic action.
(10) The composition according to (1), wherein a weight ratio of (a) and (b) is 1:30 to 25,600:1.
(11) A method for suppressing plant virus infection transmitted by winged pests, the method comprising applying, to a plant, (a) an effective amount of a glycerin acetic acid fatty acid ester and (b) an effective amount of at least one insecticidal compound selected from the group consisting of nitenpyram, dinotefuran, pyridaben, spiromesifen, buprofezin, fenpyroximate, acetamiprid, milbemectin, tolfenpyrad, flonicamid, pymetrozine, pyrifluquinazone, and salts thereof.
(12) The method according to (10), wherein (b) is nitenpyram, pyridaben, buprofezin, fenpyroximate, milbemectin, or a salt thereof.
(13) The method according to (10), wherein (b) is buprofezin and fenpyroximate or a salt(s) thereof.
(14) The method according to (10), wherein the winged pests are whiteflies.
(15) The method according to (10), wherein the winged pests are sweetpotato whiteflies.
(16) The method according to (10), wherein the winged pests are resistant sweetpotato whiteflies.
(17) The method according to (10), wherein the plant as the application target is cherry tomato or tomato.
(18) The method according to (10), wherein the plant virus is tomato yellow leaf curl virus.
(19) The method according to (10), characterized in that (a) and (b) are applied to the plant in advance.
(20) The method according to (10), wherein (a) is applied in an amount of 400 to 12,800 ppm, and (b) is applied in an amount of 0.5 to 12,000 ppm.

EXAMPLES

Examples will be described below to describe the present invention in more details. However, the present invention is by no means limited thereto.

Test Example 1

Seedlings of cherry tomatoes (cultivar: 'YellowPear') were transferred to small pots and grown until 2- to 2.5-leaf stages. A chemical having been adjusted to a predetermined concentration by dilution was sprayed thereon in a sufficient amount (the amount was such that the chemical solution dripped from the leaves), and the plants on which the diluted chemical has been sprayed were dried under a shielded condition in a greenhouse. In an aluminum-made large test container (length×width×height =68×44×82 cm, the upper surface and four side surfaces thereof are present as mesh surfaces for aeration), 16 pots containing the chemical-sprayed cherry tomatoes were equally arranged, and installation stands for releasing adult sweetpotato whiteflies were arranged at two positions on a diagonal line in the container. Chemical-resistant adult sweetpotato whiteflies to chemicals such as organophosphorus insecticides, carbamate insecticides, synthetic pyrethroid insecticides, ecdysis regulating insecticides, and neonicotinoid insecticides (hereinafter, chemical resistant adult sweetpotato whiteflies is simply referred to as adult sweetpotato whiteflies) were released for 3 days to suck a cherry tomato for TYLCV acquisition, so that the whiteflies were acquired TYLCV. Note that the chemical-resistant adult sweetpotato whiteflies used were kindly provided from Kumamoto Agricultural Research Center. The cherry tomato leaves were cut out together with the adult sweetpotato whiteflies settled on the infected cherry tomato, and equally left on the two flying sources in the aluminum-made container. After the leaves wither up, the adult sweetpotato whiteflies spontaneously spread inside the test container. The adult sweetpotato whiteflies were equally scattered to the two flying sources such that the number of individuals released was approximately 1 or 2.5 per plant (e.g.: in the case where the number of the adult sweetpotato whitefly individuals is approximately 1 per plant, 8 whiteflies×2 positions=16 whiteflies in the test container). The release period was set to 7 days. In conducting the test, any test chemical was at a practical concentration. Specifically, used were an emulsion containing a glycerin acetic acid fatty acid ester as an active ingredient (the compound A) (dilution: 500 fold, final concentration: 1600 ppm) as well as a flowable containing pyridaben as an active ingredient (product name: SANMITE FL, manufactured by Nissan Chemical Industries, Ltd.) (dilution: 1000 fold, final concentration 200 ppm), a water soluble powder containing nitenpyram as an active ingredient (product name: BESTGUARD SP, manufactured by Sumitomo Chemical Industry Company Limited) (dilution: 1000 fold, final concentration: 100 ppm), a flowable containing buprofezin and fenpyroximate as active ingredients (product name: APPLAUD ACE FL, manufactured by Nihon Nohyaku Co., Ltd.) (dilution: 1000 fold, final concentration: buprofezin 200 ppm +fenpyroximate 40 ppm), and an emulsion containing milbemectin as an active ingredient (product name: KOROMITE EC, manufactured by Mitsui Chemicals, Inc.) (dilution: 1500 fold, final concentration: 6.7 ppm) (hereinabove, the compounds B). The compound A used was the product name RIKEMAL PL-004 (glycerin diacetomonolaurate; manufactured by RIKEN VITAMIN Co., Ltd.). Moreover, in each test plot, the compound A was used together with a fatty acid ppm) (hereinabove, the compounds B). The compound A used was the product name RIKEMAL PL-004 (glycerin diacetomonolaurate; manufactured by RIKEN VITAMIN Co., Ltd.). Moreover, in each test plot, the compound A was used together with a fatty acid polyglyceride (diglycerin monooleate; product name DO-100; manufactured by RIKEN VITAMIN Co., Ltd.), which is an adjuvant used in the formulation. Note that after 80 parts by weight of the compound A and 20 parts by weight of the compound B were heated, the test chemicals were sufficiently mixed.

After the release period ended, all the adults on the cherry tomato leaves were removed. The cherry tomato leaves were placed in a biotron (25° C.) with no adult whiteflies for 30 days. The presence or absence of the infection was examined according to both PCR using the TYLCV specific primer and the cherry tomato symptom.

Determined values of percentages of TYLCV infection suppressed were each determined by dividing the number of non-infected plants by the total number of plants (16 plants). Table 1 shows the test result.

(1) Corrected value:

$$\{((100-\text{the determined value of the untreatment})-(100-\text{the determined value of the test chemical}))/(100-\text{the determined value of the untreatment})\}\times 100$$

(Note that if the value obtained from the above formula was smaller than 0, the corrected value was determined as 0.)

(2) Theoretical value:

$$(\text{the corrected value of the compound A}+\text{the corrected value of the compound B})-(\text{the corrected value of the compound A}\times\text{the corrected value of the compound B})/100$$

For example, the corrected values and the theoretical value in the test plot 3 are obtained as follows.

The corrected value of the percentage of plants infected with TYLCV in using the compound A alone=(((100−43.8)−(100−50))/(100−43.8))×100=11.1%

The corrected value of the percentage of plants infected with TYLCV in using APPLAUD ACE FL alone=(((100−43.8)−(100−6.3))/(100−43.8))×100=0%

The effect of suppressing TYLCV infection in the case of using the compound A and APPLAUD ACE FL (theoretical value)=(11.1+0)−(11.1×0)/100=11.1%

If the percentage of infection suppressed (corrected value) of a combination of two active ingredients (the compound A and the compound B) was higher than the percentage of infection suppressed (theoretical value) which was calculated from the percentages of infection suppressed (corrected values) of each of the two active ingredients, it was determined that a remarkable infection suppressing effect was exhibited. The result revealed that, in all of the test plots

TABLE 1

| Test plot | Test chemical Chemical name | Dilution magnification | Percentage of TYLCV infection suppressed* Determined value | Corrected value | Theoretical value | The number of whiteflies released (whiteflies/plant) |
|---|---|---|---|---|---|---|
| 1 | SANMITE FL | 1000 | 68.8 | (44.4) | — | 2.5 |
|   | SANMITE FL + compound A | 1000 + 500 | 93.8 | (88.9) | 50.6 |   |
| 2 | BESTGUARD SP | 1000 | 56.3 | (22.2) | — | 2.5 |
|   | BESTGUARD SP + compound A | 1000 + 500 | 87.5 | (77.8) | 30.9 |   |
| 3 | APPLAUD ACE FL | 1000 | 6.3 | (0) | — | 2.5 |
|   | APPLAUD ACE FL + compound A | 1000 + 500 | 87.5 | (77.8) | 11.1 |   |
| 4 | KOROMITE EC | 1500 | 25.0 | (0) | — | 1.0 |
|   | KOROMITE EC + compound A | 1500 + 500 | 87.5 | (83.3) | 50.0 |   |
| 5 | compound A | 500 | 62.5 | (50.0) | — | 1.0 |
|   | untreatment | — | 25.0 | — | — |   |
| 6 | compound A | 500 | 50.0 | (11.1) | — | 2.5 |
|   | untreatment | — | 43.8 | — | — |   |

Corrected values and theoretical values of the test chemicals in the test plots 1 to 3 were calculated using the determined values of the compound A and the untreatment in the test plot 6. Moreover, corrected values and a theoretical value of the test chemicals in the test plot 4 were calculated using the determined values of the compound A and the untreatment in the test plot 5. Table 1 shows the result.

The calculation methods for the corrected values and the theoretical values are as follows.

1 to 4, the compositions having the compound A and the compound B in accordance with the present invention had a remarkable infection suppressing effect.

The present inventor had observed that even when the compound A was sprayed, adult whiteflies survived one week thereafter. Nevertheless, this test revealed that when the sweetpotato whiteflies were released for 7 days on the cherry tomato leaves sprayed with the compound A, the TYLCV infection was suppressed to some extent (Table 1). It was also revealed that this effect was greatly enhanced by the combination with the compound B (Table 1). From the above, it is conceivable that the present invention greatly enhances the effect of suppressing plant virus infection attained by the compound A.

INDUSTRIAL APPLICABILITY

The method and the composition of the present invention make it possible to remarkably suppress plant virus infection of crops. Thus, the method and the composition of the present invention are industrially quite useful.

The invention claimed is:

1. A method for suppressing plant virus infection transmitted by winged pests, the method comprising applying, to a crop, a composition comprising:
   (a) a glycerin acetic acid fatty acid ester represented by formula (I):

$$CH_2OCO(CH_2)_l\text{—}CH_3$$
   $$CHOCO(CH_2)_m\text{—}CH_3$$
   $$CH_2OCO(CH_2)_n\text{—}CH_3 \quad (I)$$

wherein l is an integer of 0 to 16, m is an integer of 0 to 16, n is an integer of 0 to 16, and one or two of l, m, and n are 0; and
   (b) at least one insecticidal compound selected from the group consisting of nitenpyram, dinotefuran, pyridaben, spiromesifen, buprofezin, fenpyroximate, acetamiprid, milbemectin, tolfenpyrad, flonicamid, pymetrozine, pyrifluquinazone, clothianidin, imidacloprid, thiamethoxam, sulfoxaflor, pyridalyl, cyclaniliprole, chlorantraniliprole, cyantraniliprole, fenpropathrin, fenitrothion, ethofenprox, teflubenzuron, thiacloprid, lufenuron, spirotetramat, pyriproxifen, hydroxypropyl starch, saccharified reduced starch, sodium oleate, flupyradifurone, triflumezopyrim, tetraniliprole, fluxametamide, broflanilide, spinetoram, pirimiphos-methyl, emamectin benzoate, methidathion, chinomethionate, cartap, thiocyclam, spinosad, novaluron, lepimectin, acequinocyl, fenbutatin oxide, tebufenpyrad, DBEDC, chlorfluazuron, and salts thereof.

2. The method according to claim 1, wherein the insecticidal compound is at least one selected from the group consisting of nitenpyram, dinotefuran, pyridaben, spiromesifen, buprofezin, fenpyroximate, acetamiprid, milbemectin, tolfenpyrad, flonicamid, pymetrozine, pyrifluquinazone, and salts thereof.

3. The method according to claim 1, wherein the winged pests are whiteflies.

4. The method according to claim 1, wherein the winged pests are sweetpotato whiteflies (Bemisia tabaci).

5. The method according to claim 1, wherein the crop is cherry tomato or tomato.

6. The method according to claim 1, wherein the plant virus is tomato yellow leaf curl virus.

7. The method according to claim 1, wherein the composition is applied to the crops before winged pests fly to the crops.

8. The method according to claim 2, wherein the insecticidal compound is at least one selected from nitenpyram, pyridaben, buprofezin, fenpyroximate, milbemectin, and salts thereof.

9. The method according to claim 2, wherein the insecticidal compound is pyridaben or a salt thereof.

10. The method according to claim 2, wherein the insecticidal compound is nitenpyram or a salt thereof.

11. The method according to claim 2, wherein the insecticidal compound is buprofezin and fenpyroximate or salt(s) thereof.

12. The method according to claim 2, wherein the insecticidal compound is milbemectin or a salt thereof.

13. The method according to claim 2, wherein the winged pests are whiteflies.

14. The method according to claim 2, wherein the winged pests are sweetpotato whiteflies (Bemisia tabaci).

15. The method according to claim 2, wherein the crop is cherry tomato or tomato.

16. The method according to claim 2, wherein the plant virus is tomato yellow leaf curl virus.

* * * * *